(12) United States Patent
Oda

(10) Patent No.: US 6,761,859 B1
(45) Date of Patent: Jul. 13, 2004

(54) AIR CLEANER

(75) Inventor: Yasuhiro Oda, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/546,173

(22) Filed: Apr. 11, 2000

(30) Foreign Application Priority Data

Sep. 14, 1999 (JP) .......................................... 11-260723

(51) Int. Cl.⁷ .............................................. B01J 19/08
(52) U.S. Cl. .................................... 422/186.3; 422/121
(58) Field of Search .............................. 422/186.3, 121

(56) References Cited

U.S. PATENT DOCUMENTS

| 5,078,971 A | 1/1992 | Matuda et al. |
| 6,074,748 A | * 6/2000 | Ogata ......................... 422/121 |

FOREIGN PATENT DOCUMENTS

| JP | 9-252992 | 9/1997 |
| JP | 10-212203 | 8/1998 |
| JP | 10-314544 | * 12/1998 |
| JP | 11-104226 | 4/1999 |
| JP | 11-198640 | 7/1999 |
| JP | 2000-21216 | 1/2000 |
| JP | 2000-60955 | 2/2000 |

OTHER PUBLICATIONS

European Search Report (Mailed Sep. 16, 2002).

* cited by examiner

*Primary Examiner*—K. Mayekar
(74) *Attorney, Agent, or Firm*—Rader, Fishman & Grauer PLLC

(57) ABSTRACT

An air cleaner having a first photocatalyst carrying member (26) carrying a photocatalyst for cleaning air upon being irradiated with light, a lamp (12) for illuminating the first photocatalyst carrying member (26), and a receiving member (17) receiving a portion between the ends of the lamp (12) through the first photocatalyst carrying member (26). The first photocatalyst carrying member (26) is contained in a containing section (20) of a main body casing (15), for example, and is interposed between the lamp (12) and an innermost portion (21) of the containing section (20). The receiving member (17) may be a projection (24), for example, provided in a standing posture in the innermost portion (21) of the containing section (20).

17 Claims, 4 Drawing Sheets

AIR CLEANER

TECHNICAL FIELD

The present invention relates generally to air cleaners for cleaning air, and more particularly, to an air cleaner having a cleaning function for cleaning contaminants such as an odorous component in air using a photocatalyst.

BACKGROUND ART

In an air cleaner utilizing a photocatalyst, a lamp for activating the photocatalyst is provided. For the lamp, a cold cathode ray tube having a small diameter, for example, is utilized. The lamp is supported at only its ends in a state where it is spaced a predetermined distance apart from a photocatalyst carrying member.

The air cleaner utilizing the photocatalyst generally comprises a pre-filter for removing dust or the like in air. It must be maintained, for example, cleaned for each predetermined time period. The photocatalyst carrying member carrying the photocatalyst and the lamp are also maintained, as required. In order to clean or replace, for example, the lamp or the like inside the air cleaner, therefore, a maintenance opening is provided. When the opening is opened, the inside of the air cleaner is opened, so that the lamp or the like is touched from outside.

However, it is assumed that an inexperienced user or serviceman uselessly pushes the lamp at the time of maintenance. However, the lamp is supported on only the ends. If the center of the lamp is strongly pushed, therefore, the lamp may be deflected and damaged. Particularly when the cold cathode ray tube is utilized as the lamp, the lamp is liable to be damaged because it has a small diameter.

DISCLOSURE OF INVENTION

An object of the present invention is to provide an air cleaner capable of restraining or preventing the deformation or the damage of a lamp.

An air cleaner according to the present invention is an air cleaner comprising a photocatalyst carrying member carrying a photocatalyst for cleaning air upon being irradiated with light, and a lamp for illuminating the photocatalyst carrying member, wherein the photocatalyst carrying member includes an innermost-side photocatalyst carrying member arranged in an innermost area in the direction in which air flows, for example, and there is provided a receiving member receiving a portion between the ends of the lamp through the innermost-side photocatalyst carrying member. The lamp may be a longitudinal one or of a surface light source type. The air cleaner may further comprise a main body casing having a containing section opened at the time of maintenance, and the innermost-side photocatalyst carrying member may be contained in the containing section.

According to the present invention, when the lamp is pushed at the time of maintenance, it is possible to restrain the deflection of the intermediate portion of the lamp. Accordingly, the lamp can be prevented form being damaged.

A pressing load applied to an arbitrary position of the lamp can be received upon being distributed in a wide range by the innermost-side photocatalyst carrying member. Accordingly, it is possible to further restrain the deflection of the lamp.

Furthermore, a photocatalyst carrying member which is a constituent element indispensable for the air cleaner is also used to restrain the deflection of the lamp. Accordingly, the construction of the air cleaner can be prevented from being complicated.

It is preferable that the innermost-side photocatalyst carrying member is brought into contact with at least one of the lamp and the receiving member (preferably both of them).

According to this construction, the deflection of the lamp by a small pressing load can be restrained. Accordingly, it is possible to further restrain the deflection of the lamp. Further, the thickness in the depth direction of the air cleaner can be decreased. Therefore, the construction is preferable to miniaturizing the air cleaner.

It is preferable that the receiving member comprises a projection provided in a standing posture in the innermost portion of the containing section.

According to this construction, an air current can be ensured around the projection in the innermost portion of the containing section while restraining the deflection of the lamp by a simple structure formed by a projection.

It is preferable that the photocatalyst carrying member further comprises a front-side photocatalyst carrying member arranged short of the lamp in the containing section. In this case, it is preferable that a lattice-shaped pressing member for mounting the front-side photocatalyst carrying member on the main body casing is provided along a front surface of the front-side photocatalyst carrying member.

According to this construction, the front-side photocatalyst carrying member and the pressing member protect the front of the lamp. Consequently, it is possible for the lamp to receive the pressing load. Accordingly, the lamp can be more reliably prevented from being damaged.

It is preferable that the pressing member comprises a rib extending in a direction parallel to the lamp with the front-side photocatalyst carrying member interposed therebetween.

According to this construction, the rib receives the pressing load applied from an area just ahead of the lamp. Accordingly, it is possible to reduce the pressing load received by the lamp. As a result, the lamp can be more reliably prevented from being damaged.

It is preferable that the lamp is in contact with the front-side photocatalyst carrying member.

According to this construction, the front-side photocatalyst carrying member can be held by the lamp and the pressing member. Accordingly, a structure for holding the front-side photocatalyst carrying member can be simplified. Further, the length in the depth direction of the air cleaner can be decreased. Accordingly, the construction is preferable to miniaturizing the air cleaner.

It is preferable that the lamp comprises a lamp main body formed in a columnar shape for emitting light, and a protective cylinder surrounding the lamp main body a predetermined distance apart therefrom and transmitting the light from the lamp main body.

According to this construction, the protective cylinder can protect the lamp main body. When the lamp receives the pressing load, the pressing load is received by the protective cylinder. Accordingly, the pressing load applied to the lamp main body can be reduced by receiving the pressing load from the protective cylinder. Consequently, the lamp main body can be prevented from being damaged.

When it is difficult to ensure the light diffusion distance by bringing the photocatalyst carrying member and the lamp into contact with each other, the diffusion distance can be ensured between the lamp main body and the protective cylinder. Accordingly, a wide range of the photocatalyst carrying member can be irradiated with the light from the lamp main body.

An air cleaner according to another aspect of the present invention is an air cleaner comprising a photocatalyst carrying member carrying a photocatalyst for cleaning air upon being irradiated with light, and a lamp for irradiating the photocatalyst carrying member with light, wherein the lamp is in contact with the photocatalyst carrying member.

According to the present invention, the lamp and the photocatalyst carrying member are in contact with each other. Consequently, the lamp can be prevented from being deformed by the photocatalyst carrying member itself.

It is preferable that the lamp is interposed between the two photocatalyst carrying members, and is in contact with at least one of (preferably both of) the photocatalyst carrying members.

According to this construction, the lamp is interposed between the two photocatalyst carrying members. Even when the lamp receives a larger load, therefore, the lamp can be prevented from being deformed.

The foregoing and other objects, features, aspects and advantages of the present invention will become more apparent from the following detailed description of the present invention when taken in conjunction with the accompanying drawings.

MODES FOR CARRYING OUT THE INVENTION

Figure 1:
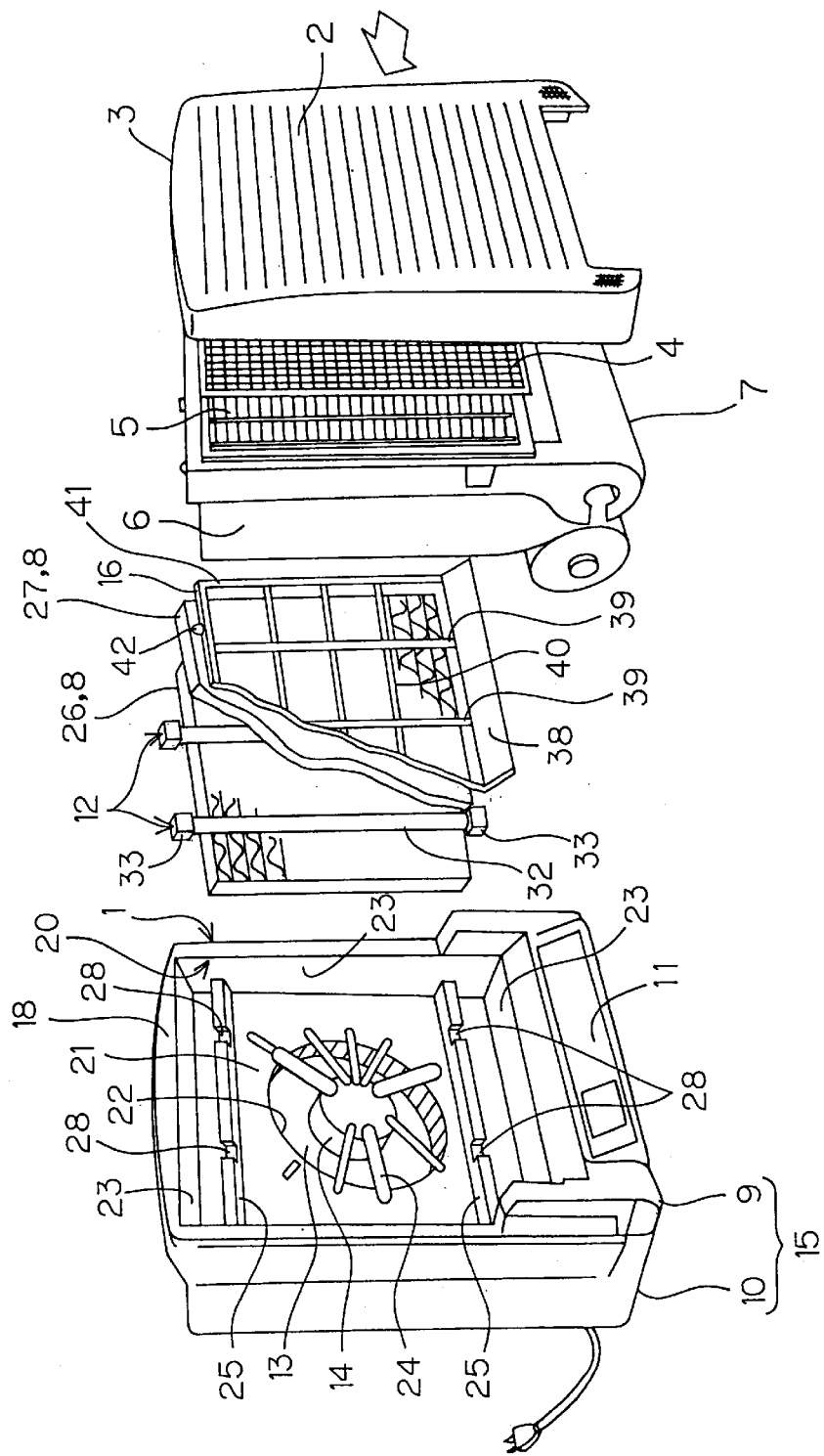
FIG. 1 is an exploded perspective view of an air cleaner according to an embodiment of the present invention.

FIG. 1 is an exploded perspective view of an air cleaner according to an embodiment of the present invention. As to the directions in the following description, a state where the air cleaner is viewed from the front is used as a basis.

In the air cleaner, the forefront of an air cleaner main body 1 is covered with a front panel 3 provided with a suction grille 2. Air is sucked into the air cleaner main body 1 through the suction grille 2.

A containing section 20 is formed on a front surface 18 of the air cleaner main body 1. A filter case 7 is contained so as to be attachable and detachable in the containing section 20. A pre-filter 4 for removing relatively large refuge or dust, an ionization section 5 for inducing discharges to charge dirty particles, and a roll filter 6 serving as a dust collecting section are mounted on the filter case 7. Further, a pair of honeycomb-shaped photocatalyst carrying members 8 carrying, on its surface or in its innerpart, a photocatalyst for cleaning contaminants upon being irradiated with light such as ultraviolet rays, one or a plurality of lamps 12 for irradiating the photocatalyst carrying members 8 with light, and a pressing member 16 for mounting the photocatalyst carrying members 8 on the containing section 20, are mounted so as to be attachable and detachable on a part, on the innermost side of the filter case 7, of the containing section 20. In the present embodiment, two lamps 12 are mounted.

The front surface 18 of the air cleaner main body 1 is constituted by a front casing 9. The containing section 20 is formed in the front casing 9. An operation panel 11 having various operation switches and various display portions is provided below the front casing 9. A main body casing 15 in the air cleaner main body 1 is constituted by the front casing 9 and a rear casing 10 mounted on the rear thereof. The front casing 9 and the rear casing 10 are combined with each other in a box shape, to form an air duct in which air flows.

An opening 22 is formed near the center of an innermost portion 21 of the containing section 20. An air fan 13 and a motor 14 for driving the air fan 13 are mounted inside the opening 22.

In the air cleaner, room air sucked in through the suction grille 2 flows backward, and is cleaned through the pre-filter 4, the ionization section 5, the roll filter 6, and the photocatalyst carrying members 8 during the flow. Air thus cleaned is blown off from a blow-off louver (not shown) provided above the air cleaner main body 1 by the air fan 13 after passing through the opening 22.

The pre-filter 4, the ionization section 5, the roll filter 6, and so forth require maintenance such as cleaning. Therefore, the above-mentioned front panel 3 is mounted so as to be attachable and detachable on the front surface 18 of the air cleaner main body 1. At the time of maintenance, a worker is positioned in front of the air cleaner, to perform work from an area short of, that is, ahead of the air cleaner. When the front panel 3 is removed, the filter case 7 can be attached and detached. Consequently, the pre-filter 4, the ionization section 5, the roll filter 6 which are mounted on the filter case 7 can be collectively attached to and detached from the air cleaner main body 1. The filter case 7 is removed, to maintain the pre-filter 4, the ionization section 5, and the roll filter 6. When the filter case 7 is removed from the air cleaner main body 1, a vent surface of the photocatalyst carrying member 8 which is mounted by the pressing member 16 is exposed in the containing section 20. When the photocatalyst carrying member 8 and the lamps 12 are maintained, the pressing member 16 is removed from the air cleaner main body 1. Thereafter, the photocatalyst carrying member 8 and the lamps 12 are removed from the containing section 20.

In the conventional construction, the lamps 12 may be damaged in the case of the above-mentioned maintenance. The reason for this is that it is assumed that the worker uselessly pushes the lamps 12, although the lamps 12 are members which are long and narrow and are liable to be damaged.

In the present embodiment, receiving members 17 receiving the lamps 12 through the photocatalyst carrying member 8 is provided in the innermost portion 21 of the containing section 20 so that the lamp 12 can be prevented from being damaged.

The lamps 12 are interposed between the two photocatalyst carrying members 8 inside the containing section 20. That is, one of the two photocatalyst carrying members 8 is an innermost-side photocatalyst carrying member 26 (a first photocatalyst carrying member) interposed between the lamps 12 and the innermost portion 21 of the containing section 20, and the other photocatalyst carrying member 8 is a front-side photocatalyst carrying member 27 (a second photocatalyst carrying member) arranged short of, that is, ahead of the lamps 12. The front-side photocatalyst carrying member 27 and the innermost-side photocatalyst carrying member 26 have the same structures, although they differ in positions inside the containing section 20. The lattice-shaped pressing member 16 for mounting the front-side photocatalyst carrying member 27 on the main body casing 15 is provided along a front surface of the front-side photocatalyst carrying member 27. The receiving members 17 include parts of a plurality of ribs 24 serving as projections provided in a standing posture in the innermost portions 21, and can receive an intermediate portions of the lamps 12 through the innermost-part photocatalyst carrying member 26.

Figure 2:
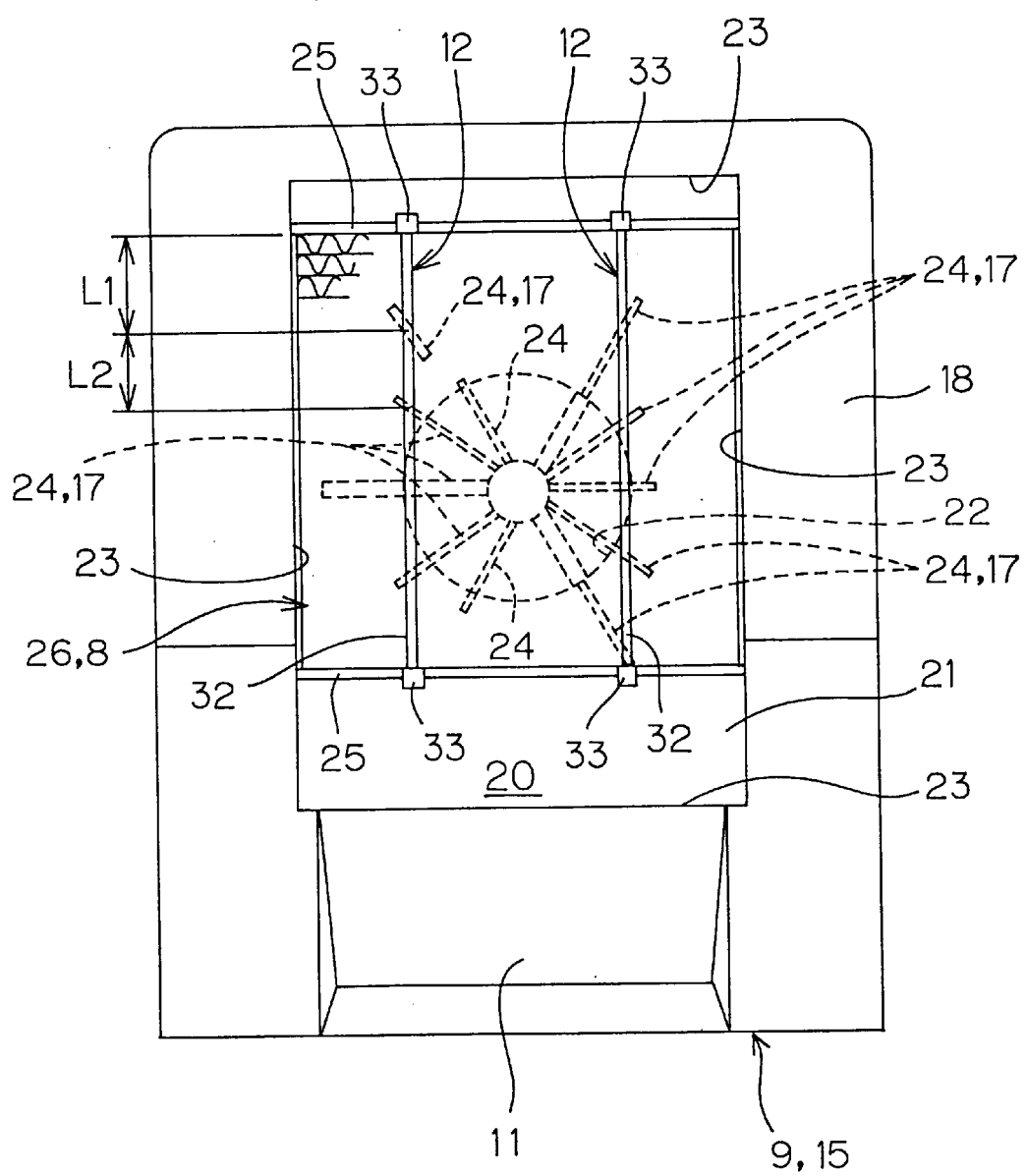
FIG. 2 is a front view of the air cleaner shown in FIG. 1, which illustrates a state where a front panel, a filter case, a front-side photocatalyst carrying member, and so forth are removed.

FIG. 2 is a front view of the air cleaner shown in FIG. 1, which illustrates a state where the front panel, the filter case, the front-side photocatalyst carrying member, and so forth are removed.

The containing section 20 is formed in the front casing 9 in the main body casing 15, and is depressed backward, while being opened forward at the time of maintenance, as described above. The containing section 20 is formed in an approximately rectangular shape as viewed from the front, and has the innermost portion 21 which is a rear surface portion and a plurality of side portions 23 extending forward from respective upper and lower and right and left peripheral edges of the innermost portion 21. The above-mentioned opening 22 is formed in the innermost portion 21, and a plurality of ribs 24 (only parts are illustrated) extending radially from the center of the opening 22 and a plurality of ribs 25 arranged above and below the opening 22 and extending in the horizontal direction are formed therein.

The ribs 24 are integrally formed in the innermost portion 21 of the containing section 20, and are formed so as to project from the innermost portion 21 by a predetermined height (a length in the depth direction). The ribs 24 are formed such that an air current can be allowed around the ribs. That is, air flowing out of the innermost-side photocatalyst carrying member 26 flows along the innermost portion 21 through a space formed inside the containing section 20 depending on the height of the ribs 24, and flows into the opening 22. At this time, the air is guided in a space inside the containing section 20 from its peripheral part toward the opening 22 at its central part along the ribs 24.

The ribs 24 include ones having only a first function of supporting the motor 14 at the center of the opening 22, ones having only a second function serving as the receiving members 17, and ones having both the first function and the second function.

The ribs 24 having the function serving as the receiving members 17 are arranged so as to be overlapped with the lamps 12, as viewed from the front. Each of the lamps 12 is overlapped with the plurality of ribs 24. The positions of the lamp 12 which are respectively overlapped with the ribs 24 (overlapped positions) are as follows. That is, the distance between the overlapped positions (L2 in FIG. 2, for example) and the distance between an end of the lamp 12 and the overlapped position close to the end (L1 in FIG. 2, for example) are predetermined distances along the length of the lamp 12, for example, not more than 50 mm. The predetermined distance is set such that the lamp 12 can be prevented from being damaged even if the lamp 12 is pushed at its intermediate position when it is supported at both its ends.

The ribs 25 are formed so as to have a predetermined height (a length in the depth direction), larger than the height of the ribs 24, from the innermost portion 21. The rib 25 is provided with recesses 28 each holding the end of the lamp 12. The ends of the lamp 12 are respectively fitted in the recesses 28 of the ribs 25, so that the lamp 12 is put in a predetermined position. The pair of upper and lower ribs 25 and the right and left side portions 23 of the containing section 20 hold a peripheral edge of the innermost-side photocatalyst carrying member 26 inside an area surrounded thereby in cooperation with each other without any displacement in the vertical and horizontal directions.

Figure 3:
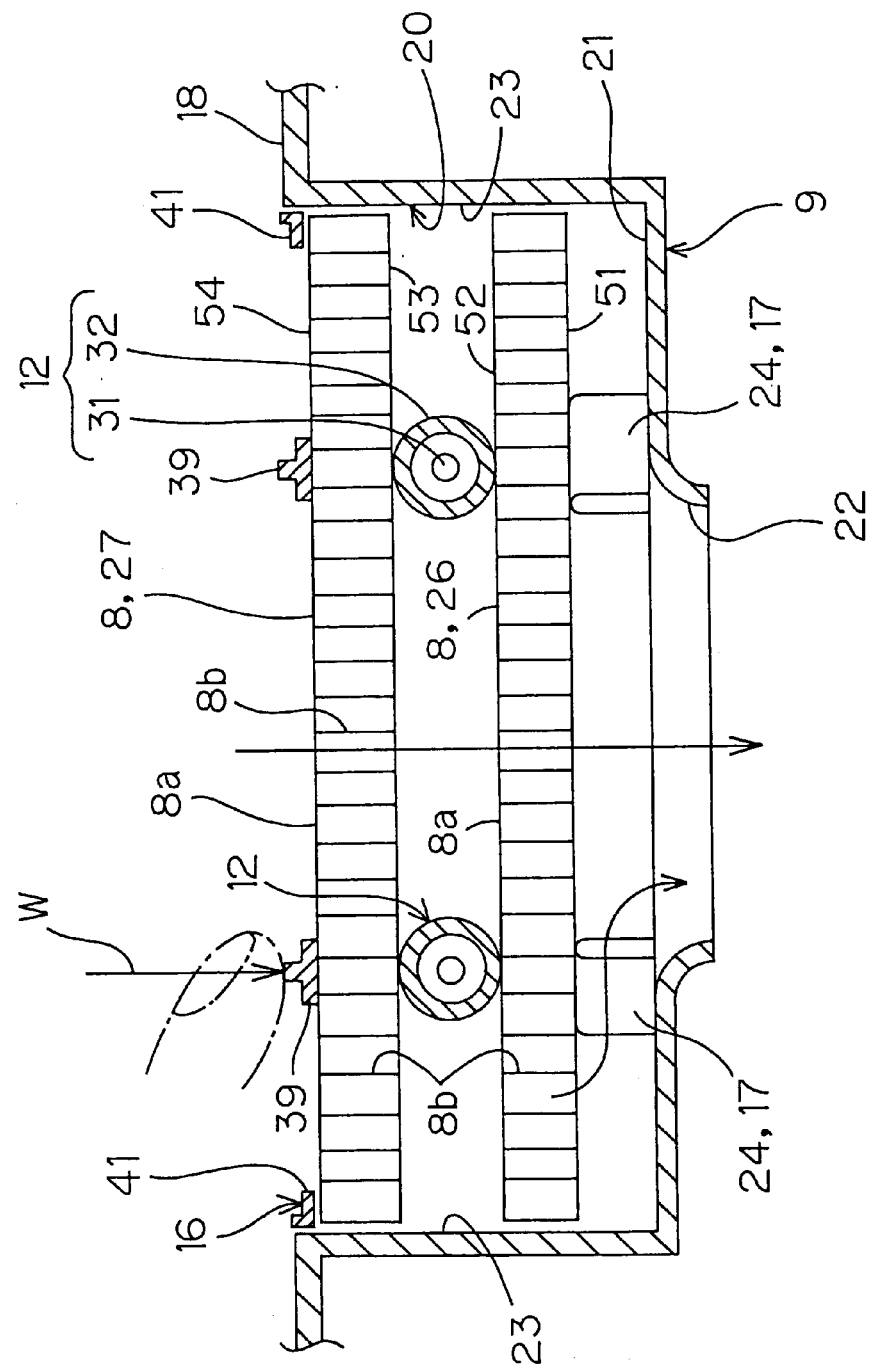
FIG. 3 is a sectional plan view of a principal part of the air cleaner shown in FIG. 1.

FIG. 3 is a sectional plan view of a principal part of the air cleaner shown in FIG. 1.

The photocatalyst carrying member 8 has a photocatalyst and a carrying member carrying the photocatalyst. The carrying member is composed of a honeycomb-shaped structure, for example, having a vent surface 8a and a lot of vent holes 8b parallel to each other which extend in a direction crossing the vent surface 8a.

The photocatalyst carrying member 8 is formed in an approximately rectangular plate shape, and is arranged so as to cross an air current inside the containing section 20.

The honeycomb-shaped structure includes a lot of flat plates parallel to each other which are formed of vinyl chloride resin, for example, and wave-shaped plates each arranged between the adjacent flat plates. The honeycomb-shaped structure is formed by alternately laminating a lot of flat plates in a strip shape and wave-shaped plates in a strip shape to form a plate having a surface and a reverse surface which extend in the direction in which the plates are laminated, and has a lot of vent holes 8b opening toward the surface and the reverse surface. A photocatalyst for decomposing the odorous component or the like upon being irradiated with ultraviolet rays is carried on the surfaces of or inside of the flat plates and the wave-shaped plates.

A photocatalyst is a material which absorbs light such as ultraviolet rays and applies its energy to a reactant to cause a chemical reaction. Examples of main functions of the photocatalyst include (a) a deodorization function by removal of an odorous component, (b) a function of decomposing contaminants which are not an odorous component, and (c) a function of sterilizing microbes and inactivating viruses (a so-called bacterial/antibacterial function). Any of the functions are achieved by an oxidation-decomposition function of the photocatalyst.

An example of a photocatalyst having an oxidation-decomposition function is titanium oxide ($TiO_2$) having an anatase-type crystal structure. Titanium oxide having an anatase-type crystal structure is preferable in that it can exhibit a high cleaning capability even by weak ultraviolet rays. Further, zinc oxide (ZnO), tungsten oxide ($WO_3$), and so forth may be used as the photocatalyst.

The lamp 12 is arranged along the vent surface 8a in the photocatalyst carrying member 8. A plurality of (for example, two) lamps 12 are arranged a predetermined distance apart from each other in the horizontal direction. The two lamps 12 are arranged such that they can illuminate nearly the whole of one of the vent surfaces 8a (surfaces), opposite to each other, of the photocatalyst carrying members 8 on both sides in cooperation with each other.

Figure 4:
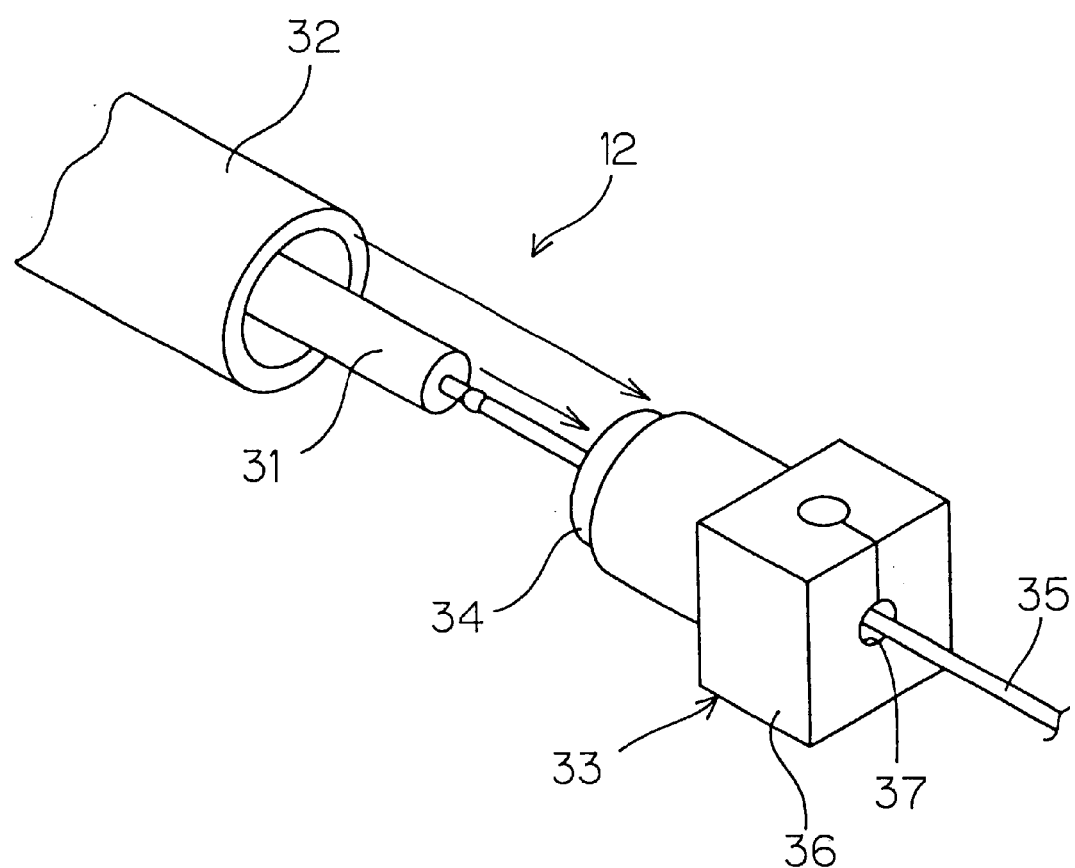
FIG. 4 is an exploded perspective view of the lamp.

As shown in FIG. 4, the lamp 12 has a lamp main body 31 formed in the shape of a longitudinal column for emitting light, a protective cylinder 32 surrounding the lamp main body 31 a predetermined distance apart therefrom and transmitting light from the lamp main body 31, and end holding members 33 mounted on ends of the protective cylinder 32. The protective cylinder 32 and the lamp main body 31 are positioned concentrically with each other by the end holding members 33. The end holding members 33 at both ends of the lamp 12 are respectively supported by the recesses 28 of the ribs 25 in the main body casing 15.

The lamp main body 31 is a straight pipe-type cold cathode fluorescent lamp in a columnar shape. The cold cathode fluorescent lamp is a fluorescent lamp or discharge lamp which operates in a regular glow discharge region by utilizing glow discharges and radiates light from a fluorescent member excited by ultraviolet rays emitted by a positive column, and can change the wavelength of the light to be radiated by selecting a fluorescent material. For example, a fluorescent material emitting light having a wavelength of 320 to 420 nm is preferable in activating a photocatalyst such as $TiO_2$ or ZnO to efficiently clean contaminants and eliminating the adverse effect on the human body. As an electrode of the cold cathode fluorescent lamp, a plate-shaped or cylinder-shaped member is used, unlike a filament used in a conventional hot cathode fluorescent lamp. The cold cathode fluorescent lamp is generally smaller in size and longer in life, as compared with the hot cathode fluorescent lamp. An example of the cold cathode fluorescent lamp is one having a diameter of 1 to 5 mm. The cold cathode fluorescent lamp is significantly thinner than a thin hot cathode fluorescent lamp having a diameter of approximately 15 mm. Further, the life of the cold cathode fluorescent lamp is long, for example, 20000 hours.

Nearly the whole of the intermediate portion of the lamp main body 31 is covered with the protective cylinder 32, and both ends of the lamp main body 31 are respectively covered with the pair of end holding members 33. Accordingly, the lamp main body 31 is protected by being covered almost completely.

The protective cylinder 32 is formed in the shape of a longitudinal cylinder whose both ends are opened, and protects the lamp main body 31 by covering the periphery thereof almost completely. The shape of the protective cylinder 32 may be the shape of a square cylinder or a prism or a cylinder having a curved surface in addition to a cylindrical member. The protective cylinder 32 may be in a shape covering a part of the lamp main body 31 by exposing the part of the lamp main body 31. An example is one in such a shape that the end of the lamp main body 31 is exposed.

The protective cylinder 32 is composed of a material capable of transmitting ultraviolet rays, for example, fluororesin, silicone resin, polyethylene resin, or polyester resin. Particularly, fluororesin is preferable as the material for the protective cylinder 32 because it is superior in ultraviolet transmission. Consequently, the protective cylinder 32 can protect the lamp main body 31 while transmitting ultraviolet rays from the lamp main body 31.

The end protective member 33 is composed of an elastic member such as a rubber material, and has a cylindrical cylinder 34, a holding section 36 for holding the cylinder 34, and a hole 37 passing through the holding section 36 and the cylinder 34. An outer peripheral surface at the end of the lamp main body 31 and an inner peripheral surface at the end of the protective cylinder 32 are respectively fitted to the inside and the outside of the cylinder 34. Consequently, the lamp main body 31 and the protective cylinder 32 are arranged concentrically with each other with a predetermined distance ensured therebetween. A lead wire 35 connected to the end of the lamp main body 31 extends from the hole 37 of the end holding member 34.

The pressing member 16 has a frame 41 opposite to a peripheral edge of the photocatalyst carrying member 8, a plate-shaped hanging portion 38 extending downward obliquely to the front from a lower end of the frame 41, a plurality of longitudinal ribs 39 formed inside the frame 41 and extending in the vertical direction, and transverse ribs 40 formed inside the frame 41 and extending in the horizontal direction. The respective portions are integrally formed of a resin material having elasticity. The longitudinal ribs 39 and the transverse ribs 40 in the pressing member 16 are formed in a lattice shape. Air flows between lattices so that the air flows into the front-side photocatalyst carrying member 27. The longitudinal ribs 39 extend in a direction parallel to the lamp 12 with the front-side photocatalyst carrying member 27 interposed therebetween. The longitudinal ribs 39 are formed in portions whose number corresponds to the number of lamps 12, for example, two portions, and are respectively arranged at positions just ahead of the lamps 12. On the other hand, the longitudinal ribs 39 are continuously formed in a length stretching nearly the full length of the lamp 12.

The hanging portion 38 in the pressing member 16 is inserted into a lower part of the containing section 20, and an engaging tongue member 42 (see FIG. 1) provided at an upper end of the frame 41 is fitted in an engaging hole (not shown) formed in an upper part of the containing section 20, so that the pressing member 16 is mounted on a predetermined position inside the containing section 20. In a state where the pressing member 16 is mounted on this predetermined position, the front-side photocatalyst carrying member 27, the innermost-side photocatalyst carrying member 26, and the lamp 12 are in contact with their adjacent member, and are interposed between a rear surface of the pressing member 16 and the tops of the ribs 24. Particularly, even in a state where no pressing load is exerted on the intermediate portion of the lamp 12, a front surface 52 of the innermost-side photocatalyst carrying member 26 and a rear surface 51 of the innermost-side photocatalyst carrying member 26 are always brought into contact with the rear of the protective cylinder 32 in the lamp 12 and the top at the front of the receiving member 17, respectively. The protective cylinder 32 of the lamp 12 is also always brought into contact with not only the front surface 52 of the innermost-side photocatalyst carrying member 26 but also a rear surface 53 of the front-side photocatalyst carrying member 27 even in a state where no pressing load is exerted on the intermediate portion of the lamp 12. Further, a front surface 54 of the front-side photocatalyst carrying member 27 is brought into contact with the whole of the rear surface of the pressing member 16.

A pressing load from an area ahead of the lamp 12 (see a force W in FIG. 3) is received by the receiving member 17 through the pressing member 16, the front-side photocatalyst carrying member 27, the lamp 12, and the innermost-type photocatalyst carrying member 26.

When the pressing load is applied to an area just ahead of the lamp 12 and just ahead of the receiving member 17, the above-mentioned sections are hardly deflected, and the lamp 12 is also hardly deflected.

When the pressing load is applied to an area just ahead of the lamp 12 and between the receiving members 17 (referred to as an intermediate portion load), the elements 16, 27, 12, and 26 may, in some cases, be slightly deflected backward at a position where the pressing load is applied. However, the elements 16, 27, 12, and 26 are overlapped with each other, so that the flexural rigidity is high as a whole. Accordingly, the maximum amount of deflection is significantly smaller, as compared with that in a case where there are no elements 16, 27, 26, and a pressing load is received by only the lamp 12. As a result, the lamp 12 may not be damaged against a pressing load normally assumed.

Furthermore, when the pressing load is applied to a position shifted from the lamp 12, as viewed from the front, the maximum amount of deflection which occurs in the lamp 12 is smaller, as compared with that in the case of the intermediate portion load, which presents no problems.

As described in the foregoing, according to the present embodiment, a load applied to the intermediate portion of the lamp 12 is received by the receiving member 17. When the lamp 12 is pushed at the time of maintenance, therefore, it is possible to restrain the deflection of the intermediate portion of the lamp 12. Accordingly, the lamp 12 can be prevented from being damaged.

The pressing load applied to an arbitrary position of the lamp 12 can be received by being distributed in a wide range by the innermost-side photocatalyst carrying member 26 interposed between the intermediate portion of the lamp 12 and the receiving member 17. Accordingly, it is possible to further restrain the deflection of the lamp 12.

The photocatalyst carrying member 8 which is a constituent element indispensable for the air cleaner is caused to have a function of restraining the deflection of the lamp 12. Accordingly, the construction of the air cleaner can be prevented from being complicated.

Furthermore, the innermost-part photocatalyst carrying member 26 is brought into contact with both the lamp 12 and the receiving member 17. Particularly, in a state where no pressing load is exerted, the innermost-part photocatalyst carrying member 26 is brought into contact with both the lamp 12 and the receiving member 17. Consequently, it is possible to restrain the deflection of the lamp 12 by a small pressing load. The deflection of the lamp 12 can be, of course, effectively restrained against a large pressing load. Further, a part, behind the lamp 12, of the containing section 20 can be made shorter in the depth direction, which is preferable to miniaturizing the air cleaner.

The receiving member 17 can be realized in a simple structure utilizing the projection-shaped ribs 24 provided in a standing condition in the innermost portion 21 of the containing section 20. In the present embodiment, the ribs 24 radially arranged are utilized, thereby making it possible to ensure an air current around the ribs 24 in the innermost portion 21 of the containing section 20 while restraining the deflection of the lamp 12.

The front-side photocatalyst carrying member 27 and the pressing member 16 which are positioned short of, that is, ahead of the lamp 12, to protect an area short of the lamp 12 from a worker. Consequently, the lamp 12 can be prevented from receiving the pressing load to the utmost. Accordingly, the lamp 12 can be more reliably prevented from being damaged.

Particularly, the longitudinal ribs 39 in the pressing member 16 receive the pressing load applied from the area just ahead of the lamp 12, so that it is possible to reduce the pressing load received by the lamp 12. As a result, the lamp 12 can be more reliably prevented from being damaged.

When the lamp 12 is brought into contact with the front-side photocatalyst carrying member 27, and particularly when the lamp 12 is brought into contact with the front-side-photocatalyst carrying member 27 even in a state where no pressing load is exerted, the front-side photocatalyst carrying member 27 can be held by the lamp 12 and the pressing member 16. Accordingly, a structure for holding the photocatalyst carrying member 27 can be simplified. Further, a part, ahead of the lamp 12, of the containing section 20 can be made shorter in the depth direction, which is preferable to miniaturizing the air cleaner.

When the lamp 12 has the protective cylinder 32, the protective cylinder 32 protects the lamp main body 31. Further, when the lamp 12 receives a pressing load, the pressing load is received by the protective cylinder 32, thereby making it possible to reduce the pressing load applied to the lamp main body 31. Consequently, the lamp main body 31 can be prevented from being damaged.

Furthermore, when the photocatalyst carrying member 8 and the lamp 12 are brought into contact with each other, the light diffusion distance from the lamp 12 may, in some cases, be difficult to ensure. However, the diffusion distance can be ensured between the lamp main body 31 and the protective cylinder 32. Accordingly, a wide area of the photocatalyst carrying member 8 can be irradiated with the light from the lamp main body 31.

When the lamp 12 is brought into contact with at least one of the photocatalyst carrying members 8, the lamp 12 can be prevented from being deformed by the photocatalyst carrying member 8 itself in contact with the lamp 12.

Particularly when the lamp 12 is interposed between the two photocatalyst carrying members 8, and is brought into contact with both the photocatalyst carrying members 8, the lamp 12 is interposed between the two photocatalyst carrying members 8. Accordingly, the lamp 12 can be prevented from being deformed even when it receives a larger load.

Although in the above-mentioned embodiment, the lamp 12 includes a cold cathode ray tube, it may include a hot cathode ray tube. In either case, it is similarly possible to obtain the effect of preventing the lamp from being damaged. Particularly, the present invention is preferable when the lamp 12 includes a cold cathode ray tube which is liable to be damaged.

Although the lamp 12 extends vertically, it may extend horizontally or obliquely.

Furthermore, the receiving members 17 may be one in a projection shape in addition to the ribs 24 formed integrally with the front casing 9. Further, the receiving members 17 formed separately from the front casing 9 may be mounted on the innermost portion 21 of the containing section 20.

Although the photocatalyst carrying member 8 has a honeycomb-shaped member, the present invention is not limited to the same. For example, it may be one carrying a photocatalyst in a fiber-shaped member. In order to restrain the deflection against the pressing load, however, a photocatalyst carrying member having high rigidity against the deflection of the vent surface is preferable.

Furthermore, the pressing member 16 is not limited to one in the above-mentioned shape. For example, it may have fine net-shaped lattices.

The arrangement direction of the receiving member 17, the innermost-side photocatalyst carrying member 26, the lamp 12, the front-side photocatalyst carrying member 27, and the pressing member 16 inside the containing section 20 is not limited to one in the depth direction. For example, they may be arranged in a direction from the innermost portion of the containing section 20 toward the front thereof.

Although the present invention has been described and illustrated in detail, it is clearly understood that the same is by way of illustration and example only and is not to be taken by way of limitation, the spirit and scope of the present invention being limited only by the terms of the appended claims.

The present invention claims the conventional priority benefits of Japanese Patent Application No. 11-260723 filed with the Japanese Patent Office on Sep. 14, 1999, the disclosure of which is incorporated hereinto by reference.

What is claimed is:

1. An air cleaner, comprising:

a first photocatalyst carrying member (26) carrying a photocatalyst for cleaning air upon being irradiated with light;

a lamp (12), having ends, for illuminating the first photocatalyst carrying member (26); and a receiving member (17) receiving a portion between ends of the lamp (12) through the first photocatalyst carrying member (26).

2. The air cleaner according to claim 1, further comprising a main body casing (15) having a containing section (20) configured to be opened at a time of maintenance, the first photocatalyst carrying member (26) being contained in the containing section (20), and being interposed between the lamp (12) and an innermost portion (21) of the containing section (20).

3. The air cleaner according to claim 2, wherein the receiving member (17) is provided in the innermost portion (21) of the containing section (20).

4. The air cleaner according to claim 3, wherein the receiving member (17) comprises a projection (24) provided in a standing posture in the innermost portion (21) of the containing section (20).

5. The air cleaner according to claim 1, wherein the first photocatalyst carrying member (26) is in contact with the lamp (12).

6. The air cleaner according to claim 1, wherein the first photocatalyst carrying member (26) is in contact with the receiving member (17).

7. The air cleaner according to claim 1, further comprising a second photocatalyst carrying member (27) arranged opposite to the first photocatalyst carrying member (26) with the lamp (12) interposed therebetween.

8. The air cleaner according to claim 7, wherein the second photocatalyst carrying member (27) is in contact with the lamp (12).

9. The air cleaner according to claim 7, further comprising a main body casing (15) having a containing section (20) configured to be opened at a time of maintenance, the first and second photocatalyst carrying members (27) and the lamp (12) being contained in the containing section (20).

10. The air cleaner according to claim 9, wherein there is provided a lattice-shaped pressing member (16) for mounting the second photocatalyst carrying member (27) on the main body casing (15) along a surface, opposite to the lamp (12), of the second photocatalyst carrying member (27).

11. The air cleaner according to claim 10, wherein the pressing member (16) comprises a rib (39) extending in a direction parallel to the lamp (12).

12. The air cleaner according to claim 1, wherein the lamp (12) comprises a lamp main body (31) formed in a columnar shape for emitting light, and a protective cylinder (32) surrounding the lamp main body (31) a predetermined distance apart therefrom and configured for transmitting the light from the lamp main body (31).

13. An air cleaner, comprising:

a photocatalyst carrying member (8) carrying a photocatalyst for cleaning air upon being irradiated with light; and a lamp (12) arranged in contact with the photocatalyst carrying member (8) for irradiating the photocatalyst carrying member (8) with light, the photocatalyst carrying member having a honeycomb structure and supporting a portion between ends of the lamp to prevent the deflection or bend of the lamp.

14. The air cleaner according to claim 13, wherein the photocatalyst carrying member (8) includes a first photocatalyst carrying member (26) and a second photocatalyst carrying member (27) which are arranged opposite to each other with the lamp (12) interposed therebetween.

15. The air cleaner according to claim 14, wherein the lamp (12) is in contact with at least one of the first and second photocatalyst carrying members (26, 27).

16. The air cleaner according to claim 14, wherein the lamp (12) is in contact with both the first and second photocatalyst carrying members (26, 27).

17. The air cleaner according to claim 13, wherein the lamp (12) comprises a lamp main body (31) formed in a columnar shape for emitting light, and a protective cylinder (32) surrounding the lamp main body (31) a predetermined distance apart therefrom and configured for transmitting the light from the lamp main body (31).

* * * * *